United States Patent [19]

Schafer, Jr.

[11] Patent Number: 5,420,518
[45] Date of Patent: May 30, 1995

[54] SENSOR AND METHOD FOR THE IN SITU MONITORING AND CONTROL OF MICROSTRUCTURE DURING RAPID METAL FORMING PROCESSES

[76] Inventor: Kenneth L. Schafer, Jr., Box 1, 63 Greene St., New York, N.Y. 10012

[21] Appl. No.: 125,915

[22] Filed: Sep. 23, 1993

[51] Int. Cl.$^6$ .................... G01R 27/04; B67B 7/46; B22D 46/00
[52] U.S. Cl. ..................... 324/653; 29/407; 164/4.1
[58] Field of Search ............. 324/639, 653, 222, 236, 324/234, 225; 164/4.1; 29/407

[56] References Cited

U.S. PATENT DOCUMENTS

| | | | |
|---|---|---|---|
| 2,817,813 | 12/1957 | Rowan et al. | 324/653 |
| 3,805,160 | 4/1974 | Philbrick et al. | 324/653 |
| 4,649,556 | 3/1987 | Rinik et al. | 378/71 |
| 4,797,614 | 1/1989 | Nelson | 324/653 |
| 4,820,981 | 4/1989 | Bussiere et al. | 324/222 |
| 4,833,396 | 5/1989 | Haberland | 324/653 |
| 5,142,228 | 8/1992 | Kingsburg | 324/653 |
| 5,215,603 | 6/1993 | Nakayama et al. | 324/222 |

FOREIGN PATENT DOCUMENTS

| | | | |
|---|---|---|---|
| 1469438 | 3/1989 | U.S.S.R. | 324/222 |
| 1670555 | 8/1991 | U.S.S.R. | 324/222 |

OTHER PUBLICATIONS

Terman, F. E., *Radio Engineer's Handbook*, McGraw-Hill, New York, 1943 (listed for historical value only).

Black et al., "High Temperature Superconducting Resonator For Use In Nuclear Magnetic Resonance Microscopy", Appl. Phys. Lett. 62 [7], 15 Feb. 1993.

"Electrical Steels; Past, Present and Future Developments" A. J. Moses, IEE Proceedings, Sep. 1990.

"The Effect of Aluminum on the Magnetic Properties of Lamination Steels", Hou et al., IEEE Log No. 9100960 Sep. 1991.

"Thin-Film HTS Probe Coils For Magnetic-Resonance Imaging", Withers et al., IEEE Trans. App. Supercond, 1993.

*Primary Examiner*—Maura K. Regan
*Attorney, Agent, or Firm*—Webb Ziesenheim Bruening Logsdon Orkin & Hanson

[57] ABSTRACT

An electronic resonator is employed for the on-line nondestructive measurement of microstructure, as defined by the diameter of grains of the type found in ferritic steel alloys during high rate formation processes. The quality factor (Q) of an inductive-capacitive (LC) tank circuit is determined to obtain a measure of energy dissipated in a steel alloy sample inductively coupled to it. Dissipative energy in the sample results from two sources, hysteresis and eddy currents. Eddy current loss is relatively microstructure insensitive and is mainly related to chemical composition and temperature while hysteresis loss is determined by microstructural factors. If microstructural variables other than grain size, and the factors determining eddy current loss are held constant, grain size becomes the dominant factor in differential energy loss with grain size being inversely related to hysteresis loss. Under these condition grain size is inversely related to energy dissipation and thus the measured Q of the resonant circuit.

26 Claims, 2 Drawing Sheets

SENSOR AND METHOD FOR THE IN SITU MONITORING AND CONTROL OF MICROSTRUCTURE DURING RAPID METAL FORMING PROCESSES

BACKGROUND OF THE INVENTION

1. Field of the Invention

The present innovation relates to the field of metallographic process control engineering. More specifically, it constitutes an apparatus and technique for the in situ monitoring and control of grain size as well as other microstructural variables, e.g., grain orientation, in the production of steel alloys.

2. Description of Prior Art

It has long been known to those skilled in the art that grain size is an important predictor of desirable metallurgical properties in steel products. Ductility, yield strength, tensile strength, and other physical properties of steel alloys can be predicted and controlled by the manipulation of polycrystalline grain size. In nonoriented electrical steels used in motors and transformers, etc., controlling grain size is extremely important in the production of energy efficient alloys with low "iron loss". In oriented electrical steels both grain size and orientation are important in producing a low loss alloy.

Chemical, thermal, and mechanical conditions during the milling process can greatly influence the final grain texture of the material. Specifically, mechanical deformation interacting with complex thermal sequences in particular chemical and gas atmospheric environments determines the ultimate microstructural characteristics of the metal alloy.

At the present time there is no sensor that can monitor microstructural transitions in situ for rapid metal forming processes like the production of steel. The highest volume product in the steel industry is hot rolled strip (30% of all steel shipped) which moves off the line at speeds in excess of 4500 feet per minute. The first opportunity to observe microstructural properties like grain size occurs after the fact when samples are removed from the coiled steel and sent to the laboratory for inspection by optical microscopy. If processing conditions were not optimal at any point in the milling process, an entire heat may have to be diverted to alternative use, given remedial heating, or melted down for scrap at substantial cost to the producer.

Determination of grain texture using optical microscopy to inspect polished and etched samples is a tedious and time consuming process. Thus the testing of hot and cold rolled strip, for instance, is typically limited to the inspection of samples cut from the head and tail of each coil. If on-line grain size measurements were possible, it would not only make it easier to accurately control production, but it would also permit exploration of the heuristic consequences resulting from fine tuning the complex mechanical, chemical, and thermal interactions inherent, but at this point invisible, in the steel manufacturing process.

Techniques have been described using ultrasound backscattering and X-ray diffraction to measure grain size on-line. In the case of ultrasound the time constants involved in the propagation and analysis of sound waves traveling through the steel are too long to determine grain size in the rapid metal forming processes commonly used in the production of hot or cold rolled strip. In the case of X-ray diffraction the temporal requirements of proportional X-ray counters currently available make any time-integrated intensity method, while theoretically possible, very impractical for use on the factory floor.

As an example, Renik et. al. (U.S. Pat. No. 4,649,556) simulated the conditions that would be encountered in a temper mill when measuring grain size on-line with an X-ray diffraction apparatus. The steels used in the simulation were AISI 1006 and 1008 drawing quality steels optically measured for grain size by the grain intercept method. To achieve an acceptable standard error of 20% in the X-ray determined grain size measurement for a sample moving at 1500 feet per minute and at a useful counting rate for existing technology, 100 non-overlapping segments would have to be examined. For steel moving at 4500 feet per minute which is not uncommon at the coiler, the number is 300. In this case the total analysis time for one grain size determination would be ten seconds, and in that time frame the steel strip would have moved over ⅛th of a mile. This means that the spatial resolution of such a system is 750 feet of steel strip product. None of these proposed systems is currently in use.

SUMMARY OF THE INVENTION

In accordance with the present invent ion, a technique and detector are provided for the measurement of polycrystalline ferritic microstructure during rapid movement of the material relative to a stationary observation point. An inductive-capacitive (LC) tank circuit with a quality factor (Q) substantially higher in its unloaded state than when loaded by an inductively coupled steel alloy sample, is swept through a range of pure sinusoidal frequencies that bracket and include its center or resonant frequency. It has been observed that when sample geometry, chemical composition, temperature, and sample-to-tank circuit distance are held constant, the Q of the resonant LC circuit, as measured by the above mentioned frequency sweep, accordingly defined by the equation:

$$Q = f_O/f_H - f_L \quad (1)$$

where
- $Q$ = the quality factor of the resonant circuit;
- $f_O$ = the center or resonant frequency;
- $f_H$ = the upper frequency point where transmitted peak-to-peak signal amplitude is 0.707 or 3 db below $f_O$ amplitude;
- $f_L$ = the lower frequency point where transmitted peak-to-peak signal amplitude is 0.707 or 3 db below $f_O$ amplitude;

will be inversely related to the polycrystalline grain size expressed as mean grain diameter in ASTM E-112 designation.

This invention has been made as an improvement over previous methods and apparatuses that provide for the in situ measurement and control of grain size in rapid metal forming processes. A feature of the present invention is a sensor that operates in the radio frequency portion of the electromagnetic spectrum thereby permitting a method of determining the Q of the resonant LC tank circuit and hence the grain size of a sample inductively coupled to it in a number microseconds. This makes possible a spatial resolution and temporal response factor many orders of magnitude better than is found in descriptions of prior art.

In modern hot and cold rolling mills advanced process control systems, as previously mentioned, can alter most processing parameters in slightly more than a second. If information concerning the microstructural status of the material is available, fine tuning of the whole complex sequence of chemical, mechanical, and thermal events that comprise the process can be accomplished. Reheat temperatures and cooling times, addition of chemicals in baths and gas atmospheres, rate of working or recrystallizing worked metal, and the application of coatings can all be manipulated while observing the effect in real time, as opposed to after the fact.

It is a primary objective of this invention to provide a sensor and a method for the in situ nondestructive measurement of microstructure during rapid metal forming processes.

It is a further objective of the invention to provide a method of microstructural determination which is sufficiently fast and accurate enough to be a causal agent in the real time control of rapid metal forming processes.

DESCRIPTION OF THE PREFERRED EMBODIMENTS

There is no history of using the quality factor (Q) of low radio frequency inductive-capacitive (LC) resonators to measure the microstructural characteristics of polycrystalline materials like ferritic metal alloys. An inductor stores energy in a magnetic field around the wires it is comprised of and in any magnetic material coupled to the field around the wires. A capacitor stores energy by polarizing the dielectric material between the plates. Ideally most of the stored energy is returned to the circuit, but practically there are losses due to energy dissipation in the components making up the circuit. The Q of the circuit expresses the amount of energy dissipated by the components of the circuit. The higher the Q, the less the dissipated loss.

Figure 1:
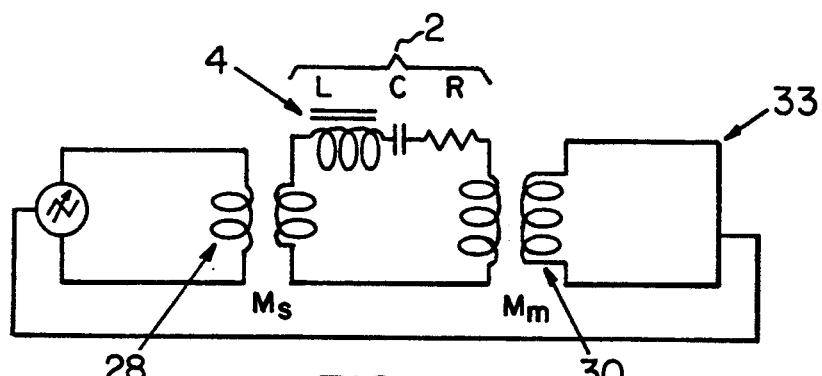
FIG. 1 is the schematic equivalent circuit diagram for a microstructure-sensing LC resonator coupled inductively to the radio frequency signal source, the sample, and the network analyzer.

As shown in FIG. 1, when a resonant LC circuit 2 that has a substantially higher Q in its unloaded state than when loaded by an inductively coupled steel alloy sample 4, the difference in energy loss, reflected in a lowered Q caused by dissipation in sample 4, can be shown to be related to microstructural characteristics of the steel sample.

Energy loss in the inductively coupled sample 4 results from two sources, induced eddy current loss, and hysteresis loss. Eddy current loss $P_E$ is classically expressed in terms of thickness of the material d, peak flux density B, the frequency of alternating current f, the resistivity of the material r, and $\eta$ the loss anomaly factor resulting from complex domain movement during the magnetizing cycle as:

$$P_E = \eta[(\pi dBf)^2/6r]W/m^3 \qquad (2)$$

Eddy current loss is determined by the chemical composition and temperature (which influences the electrical resistance) of the material (see article "Electrical Steels: Past, Present And Future Developments", A. J. Moses, IEE Proceedings, Vol. 137, Pt.A, No. 5, September, 1990). Hysteresis loss, on the other hand, is microstructure sensitive and is affected by such factors as impurities, grain texture, strain, etc. Hysteresis loss can be measured by subtracting classically calculated eddy current loss from total sample losses (see article "The Effect of Aluminum on the Magnetic Properties of Lamination Steels", Hou et. al., IEEE Log Number 9100960). Therefore if factors responsible for eddy current loss, e.g., thickness, chemical composition, and temperature are kept constant or compensated for, observed differences in energy dissipation are due to hysteresis loss and hence microstructural factors in the polycrystalline lattice of the sample 4.

Figure 2:
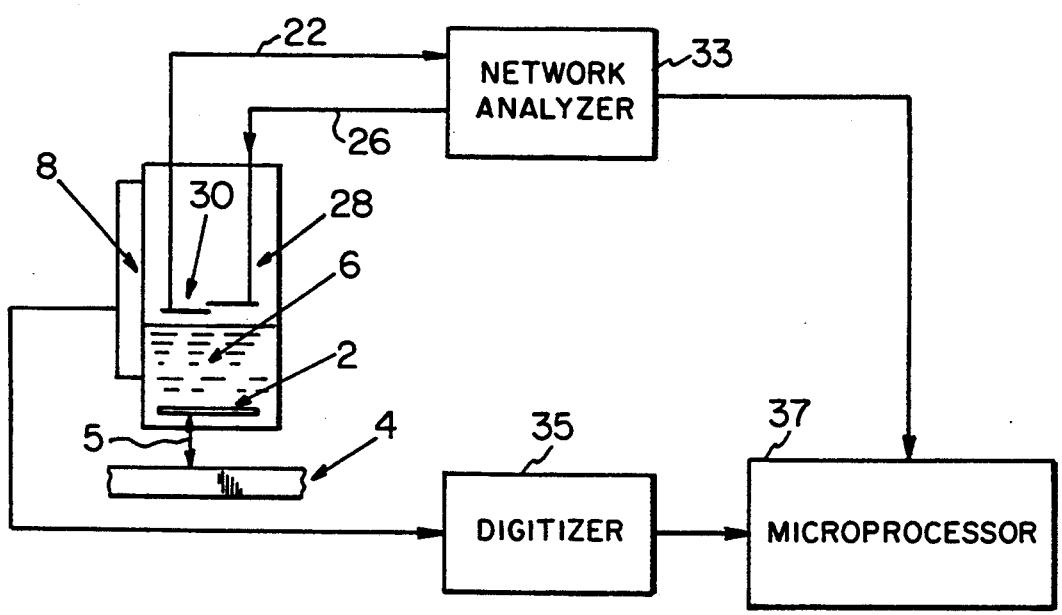
FIG. 2 is a schematic representation of a device that determines differential energy dissipation in inductively coupled sample materials by means of Q determinations.

In accordance with the present invention, the above mentioned hysteresis loss in the inductively coupled sample 4 (FIG. 1) is measured by holding constant the temperature of the elements comprising the LC tank circuit 2 by means of a liquid nitrogen bath 6 shown in FIG. 2 and measuring sample 4 temperature by a non-contacting device such as an infrared optical temperature detector 8 (FIG. 2) to calculate eddy current loss at specific sample temperatures.

A second important function of the liquid nitrogen bath 6 (FIG. 2) is that it permits the resonant LC circuit 2 to operate under superconducting conditions. The LC circuit 2 is comprised of a pair of thin film $Y_1B_2C_3O_7$ (YBCO) planar inductors separated by a dielectric substrate, (see article "Thin-Film HTS Probe Coils For Magnetic-Resonance Imaging", Withers et. al., IEEE Trans. Appl. Supercond. [ASC], 1993), which resonate at 4 MHz with a $Q > 2 \times 10^3$ when submersed in a medium which maintains its temperature below the $T_c$, critical temperature for the YBCO thin film inductor ($T_c \sim 83$ kelvins). The temperature of liquid nitrogen is 77 kelvins, comfortably below the $T_c$ for YBCO. At superconducting temperatures the YBCO thin film inductor offers almost no resistance to the flow of alternating current. Thus the main energy dissipation in the superconducting LC circuit 2 is due to electrical and/or magnetic losses in the dielectric substrate comprising the distributed capacitor. If the LC circuit is a series resonance circuit 2 as shown in FIG. 1:

$$Q = \omega L/R \qquad (3)$$

where $\omega$ is the angular frequency, L is inductance, and R is resistance at frequency $\omega$. The resonant frequency of the circuit is $\omega^2 = 1/LC$. If $\omega^2$ is in the low megahertz range, $R < 100 \ \mu\Omega$, and L, the self inductance, is about a μH; the expected Q, unloaded by the sample, will be ~$10^4$.

If the resonator were comprised of a low loss bulk copper inductor and a low loss capacitor maintained at 77 kelvins, the highest Q obtainable at low radio frequencies would be ~400, (see Terman, F. E., *Radio Engineer's Handbook*, McGraw-Hill, New York, 1943, and Black et. al.," High Temperature Superconducting Resonator For Use In Nuclear Magnetic Resonance Microscopy", Appl. Phys. Lett. 62 [7], 15 Feb., 1993). Thus the use of a superconducting LC resonator has two important implications for the electromagnetic sensing of polycrystalline metallic microstructure: 1.) The inductively coupled metallic sample can cause significant loading of a high Q superconducting resonator at much greater resonator-to-sample distances than a relatively low Q conventional LC tank circuit. 2.) The increased sensitivity of a high Q superconducting resonator to energy dissipation in an inductively coupled metallic sample increases the signal-to-noise ratio (SNR) of the sensor system and hence the ability of the sensor to discriminate microstructural properties in the sample.

Under these conditions differential sample losses are attributable to microstructural factors such as grain size, grain geometry, grain orientation, number of inclusions, strain, etc.

Figure 3:
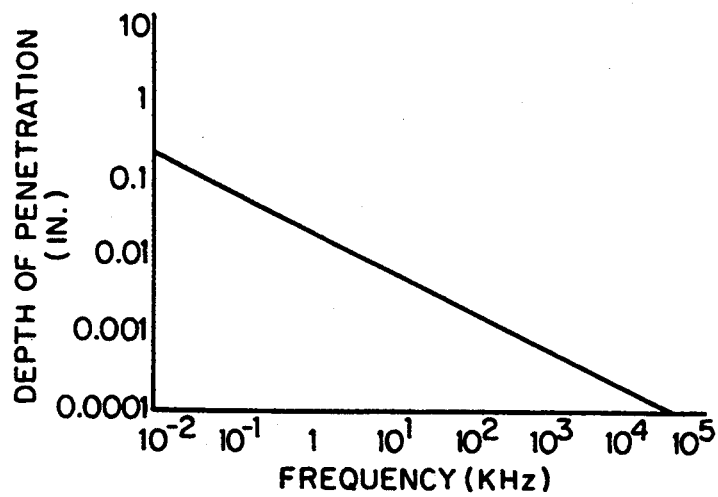
FIG. 3 is a graphical representation of the depth of penetration by electromagnetic radiation of a steel alloy surface as a function of frequency.
Figure 4:
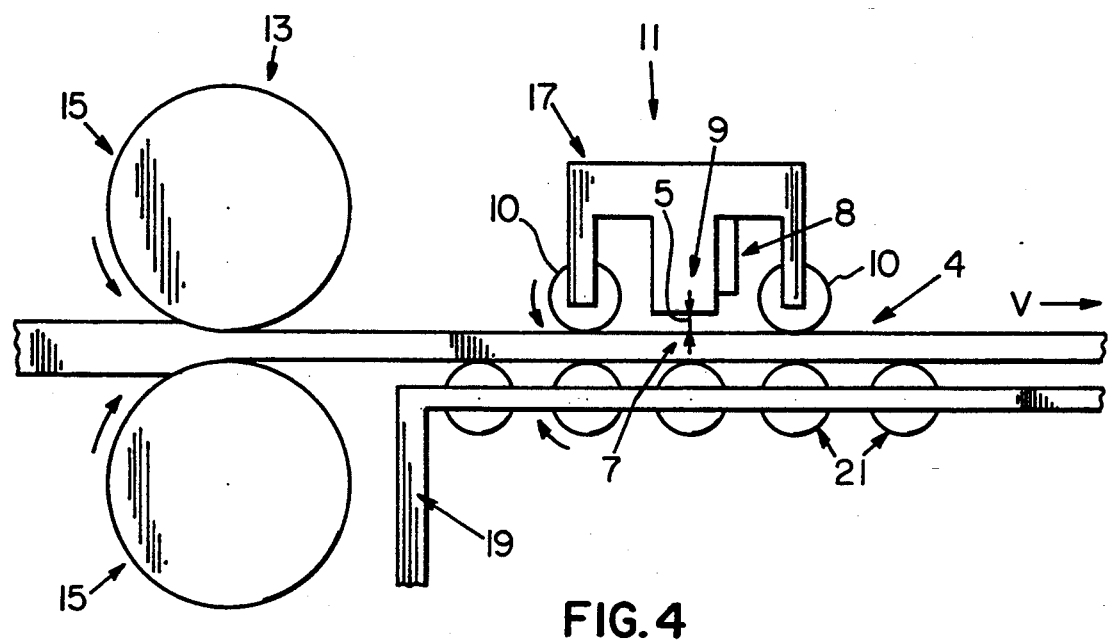
FIG. 4 is a schematic representation of a typical roll stand in a multi-stand tandem hot strip mill equipped with sensing devices for steel strip microstructure and temperature in accordance with the present invention during rolling.
Figure 5:
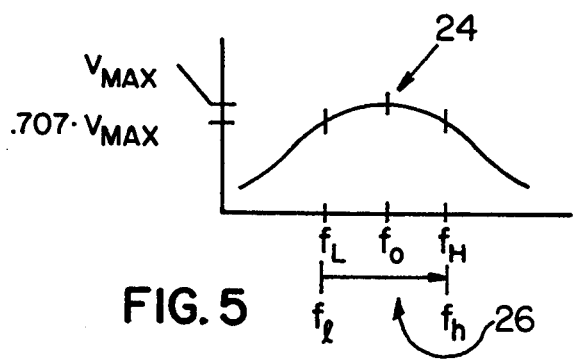
FIG. 5 is a graphical representation of peak-to-peak voltage output from an LC resonator as a function of signal frequency swept through the center frequency of the resonator.

The depth of penetration of induced currents in the sample 4 (FIG. 1) is determined by the frequency of the electromagnetic radiation as seen in FIG. 3. If the frequency is in the high kilohertz to low megahertz range penetration depth for high alloy steel will be around 0.001" or less, which is considerably less than the thickness of production steel strip. This means that sheet thickness is not a factor in differential energy loss in this situation. In situations where coatings are present, frequency can be manipulated to control penetration depth and consequently the effective depth of the measurement. Referring now to FIG. 4 there is shown a schematic representation of an in situ microstructure measuring apparatus for use on a production line for the hot or cold milling of steel with one invention embodiment indicated generally by numeral 11. The differential energy loss due to microstructural characteristics of polycrystalline samples in the form of strip, sheet, plate, bars, etc., is determined as the material travels past a test point 7. At the test point 7 the steel alloy is inductively coupled by sinusoidal electromagnetic radiation 28 (FIG. 1) of frequency $f_O$ 24 (FIG. 5) to an LC tank circuit 2 (FIG. 1) which is swept through a range of frequencies, $f_L$–$f_H$ 26 (FIG. 5) that bracket and include the resonant frequency of the LC circuit. The peak-to-peak voltage 22 (FIG. 5) received from the LC resonator by pickup coil 30 (FIG. 1) is conveyed to a network analyzer 33 (FIG. 2) for both amplitude and phase analysis. The analysis results in a determination of the Q of the LC resonator 2, at resonator-to-sample distance 5, based on either the scalar analysis for Q graphically depicted in FIG. 5 and expressed by the equation (1) for Q or a vector analysis based on both amplitude and phase information presented in polar coordinates as a Smith Chart. The Q determination is then passed to a microprocessor based computational system 37 (FIG. 2) where temperature information from 8 is converted to a digital value 35 to compensate the Q value for fluctuations in sample 4 temperature that occur during processing. The microprocessor system 37 then performs further statistical analysis, storage, and display functions before generating relevant process control signals.

While Q is the most commonly used measure of energy dissipation in an LC circuit, it should be understood that several other related measures could also be employed as a dependent measure of differential energy loss in the inductively coupled metallic sample. For a series resonant LC circuit the impedance (Z) seen by a signal source at resonant frequency is comparatively low. For a parallel LC tank circuit the impedance at resonant frequency is very high. The exact Z is determined by resistance in the circuit and the Q of the components comprising the circuit, which would of course include the energy loss in an inductively coupled sample. In the time domain, as opposed to frequency domain, the lifetime of an LC resonator response to a pulse of sinusoidal radio frequency energy at center frequency is directly related to the Q of the LC circuit. The exponential factor, $\gamma$, that describes the response decay function is thus another measure of the Q of the circuit and can be used as a dependent measure of differential energy loss in the context of the current invention.

The apparatus 11 as shown in FIG. 4 is designed for use in a hot or cold strip rolling mill with a typical roll stand 13 being represented in the schematic drawing. The roll stand includes two working rolls 15 that simultaneously elongate and reduce the thickness of the metallic strip. The steel strip moves through successive roll stands at velocity V from left to right as seen in FIG. 4 with velocity increasing as the strip is progressively elongated. The strip is moved along the line by a transfer table 19 which consists of a frame supporting a number of transfer rollers 21 that rotate to move the strip to the subsequent roll stands, the cooling table or the coiler (not shown). In some situations a reversing mill is employed and the metal strip is passed successively in alternating directions through the same roll stand for progressive reduction with the working rolls being brought closer together on subsequent passes.

Because the sensor apparatus 9 utilizes the magnetic properties of the polycrystalline metal to detect microstructure, the sensor must be placed in a hot strip mill at a point on the line where the temperature of the steel has dropped below the Curie temperature, the temperature below which the magnetic properties of the metal return. In the metallurgical literature the Curie temperature corresponds to $A_2$ the formerly designated critical temperature at 1414° F. This temperature does not involve a phase change in the steel microstructure as do $A_1$ and $A_3$ critical temperatures, but instead marks a gradual heat effect and magnetic change (1414° F.–1454° F.), ferrite being ferromagnetic below this temperature range, and paramagnetic above. In a cold rolling mill where the temperature from working the material never exceeds the Curie temperature the sensor can be placed at any point on the line. Also in continuous annealing or coating operations the sensor can be placed at any point on the line other than in the annealing furnace itself or other obviously hostile environments to monitor the polycrystalline microstructure of the steel alloy.

The sensor portion 9 of the apparatus 11 rides on a carriage equipped with pinch rollers 10 of the same type found in the transfer table, and the carriage 17 is fixed (not shown) to the transfer table at the test point 7 on the line. The carriage is fixed to the transfer table so as to pinch the horizontally moving steel between the carriage and transfer rollers thereby minimizing vertical movement of the steel strip and simultaneously fixing the resonator-to-sample distance 5 at the test point 7.

The LC resonator which is inductively coupled to the steel as it moves by the test point 7 is located on a plane parallel to, and at a distance 5 of, 25 mm from the surface of the steel strip. At this distance the radio frequency electromagnetic field on the steel surface comprises a circular target area with a diameter of ∼75 mm.

It is an important feature of this invention that the apparatus and method for monitoring microstructure in situ be sufficiently fast and accurate enough to provide useful information that can be made causal in the rapid metal forming process. As mentioned previously, the velocity of steel moving on-line at the coiler in a hot strip mill can be in excess of 4500 ft./min. This is where the test point 7 of apparatus 11 might be located in a hot strip mill as indicated earlier in the discussion of Curie temperature.

At resonator center frequency, $f_O$ 24 (FIG. 5) of 4 MHz a frequency sweep consisting of forty cycles of increasing frequency that bracket and include the center frequency 24 would take $1 \times 10^{-5}$ sec. or ten microseconds. In this period of time, which will be referred to as the test epoch, $t_e$, the steel sheet (V=4500 ft./min. or 23.44 m/sec.) will have moved 0.2344 mm. With a target area of 75 mm the target area drift during $t_e$ is 0.3%. Thus with a $t_e$ of ten microseconds and a sweep of forty cycles of increasing frequency the procedure for determining Q would be sufficiently fast for any velocities found on a hot or cold rolling production line.

At center frequency, $f_O$ 24 (FIG. 5) equal to 4 MHz and resonator-to-sample distance 5 equal to 25 mm the Q value for a steel alloy sample is roughly 1000. From the equation (1)

$$Q = f_O/f_H - f_L$$

$f_H - f_L$ would be 4 kHz. Commercially available microprocessor controlled network analyzers are more than accurate enough in both amplitude and phase domains to yield reliable Q measurement in $t_e = 10$ μsec. with a bracket sweep of slightly more than 4 kHz at a center frequency of 4 MHz.

A more important consideration in determining the in situ accuracy of the apparatus and method is vertical displacement of the horizontally moving steel and resulting changes in the resonator-to-sample distance 5 as seen in FIG. 4. The changes in the Q of the LC tank circuit 2 produced by inductive loading by the metallic sample 4 are very sensitive to resonator-to-sample distance 5, which will be referred to as $d_y$. In tests of Q as a measure of optically determined ASTM E-112 grain size, a 0.5 mm $d_y$ was found to be equivalent to 0.3 of an ASTM grain size, the obtained accuracy of the Q based measurement system 9 (FIG. 4) in static tests.

Fortunately, since a Q determination can be completed in 10 μsec. as indicated above, a large number of such measurements could be completed in the one second period that constitutes the time constant for most parameters of on-line process control systems. If a second microprocessor system 37 (FIG. 6) receives the Q determination from the network analyzer 35, and is programmed to store, average, and calculate the standard deviation, σ, of n number of successive measurements, the mean Q and standard deviation about that mean Q could be reported every second or so based on a substantial statistical analysis. The number of successive measurements, n, included in the statistical analysis is limited by data transfer rates between tile two microprocessors in 35 and 37 the slew rates in the network analyzer electronics, and the calculation times in system 37 for the statistical analysis. Using specifications for existing automated test equipment (ATE) the n for the statistical analysis would be in the thousands.

This statistical analysis would have the additional advantage of providing other microstructural information about the sample. An inclusion present in a single sample target area would produce an anomalous Q measurement, which would in turn produce a higher deviation score, σ, for the distribution of n scores. The deviation score, σ, would thus provide a measure of the frequency of inclusions in the microstructure. Likewise, a uniform coating would produce uniform internal stress in the microstructure and thus consistent Q values, but any variation in the coating would produce anomalous Q values and thus a larger σ. While the microstructural modifications of steel strip by applications of coatings has been discussed, it should be understood that other surface manipulations such as the scribing of lines perpendicular to the rolling direction, partially ablating coatings by electrical discharge, or laser etching of the steel surface and/or coatings have similar effects on the microstructural electromagnetic properties of the steel and would hence result in detectable and quantifiable differences within the scope of measurement and control of this invention. These measurements would have utility in process control systems for the cold rolling and finishing of high quality electrical steel strip.

The signal-to-noise ratio (SNR) for the detection of anomalous Q values would be determined by the amount of vertical displacement of the moving steel at the test point 7 (FIG. 4) under the carriage 17. This value would set the noise floor for σ as a measure of microstructural deviations from the mean of n successive Q determinations. An obvious variation on the embodiment 11 presented in FIG. 4 would be a single pinch roller with sensor 9 attached instead of the carriage 17. This system would lower the noise floor under certain circumstances by minimizing $d_y$ 5.

The following experiment was conducted to evaluate the accuracy of the Q measurements taken from actual production steel samples in predicting ASTM E-112 grain size determined by optical microscopy using the grain intercept method. The samples utilized in this experiment were all ultra-low carbon alloys with the following chemistry:

C 0.002
S 0.006–0.009
Mn 0.160–0.190
N 0.002–0.003
P 0.008–0.014
Al 0.001–0.006
Cu 0.010

Three of the samples were 0.0605" thick and the fourth sample was 0.0060" thick, all measuring 6"×6" square. The sensor was a YBCO thin film planar LC resonator with a center frequency of 4 MHz and a Q of 2000 when placed in a liquid nitrogen bath and coupled to a drive and pickup coil pair consisting of one turn of 1" diameter copper wire 5 cm from the resonator. The drive and pickup coils were placed beside each other in such a manner that feedthrough was minimal (about −60 db). The resonator-to-sample distance was 26 mm. Due to curvatures of different magnitude in the samples, the difference in resonator-to-sample distance was ~ ±0.5 mm.

Figure 6:
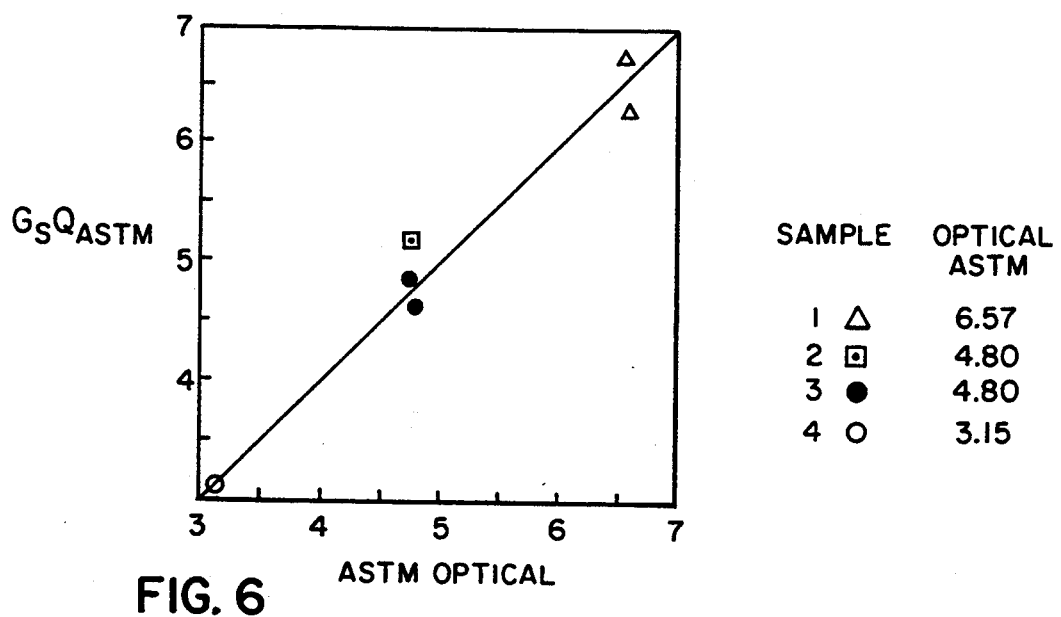
FIG. 6 is a graphical representation of the relationship between the optically determined ASTM grain size of steel plates and the Q determined grain size by the method of this invention.

The results of this experiment are presented in FIG. 6 for the four samples. In several instances multiple measures were taken and are presented to give an idea of the variability in successive measures. Two of the samples had the same optically determined ASTM grain size (4.80) and give additional information concerning the reliability of Q determined grain size measures. The relationship between Q measures and optically determined grain size is given by the equation:

$$G_S Q_{ASTM} = 13.05 - (8.6363 \times 10^{-3})$$

where $G_S Q_{ASTM}$ is the estimate of ASTM E-112 grain size based on measured Q. It can be seen from this experiment that there is good agreement between the two methods of determination and sample thickness was not a contributing factor in this situation.

Although certain preferred embodiments of the present invention have been illustrated and described herein, other embodiments will become apparent to those skilled in the art and, accordingly, the scope of the present invention should be defined only by the following claims.

I claim:

1. A method for in situ measurement and process control of polycrystalline ferritic microstructure at a number of different depths in a material comprising the steps of:
    moving the materials and a predetermined measuring point relative to one another;
    inductively coupling the material to an LC resonator by means of a pure sinusoidal radio frequency electromagnetic field as the materials and the test point travel relative to one another;
    sensing the difference in energy dissipation produced by inductively coupling the material to the LC resonator at the test point as the materials and test point travel relative to one another;
    determining the microstructural status of material using the differential quality factor, Q, of the LC circuit while inductively coupled to the sample material at the test point as a dependent variable;
    determining the temperature of the sample material by non-contacting means at the test point as the material and the test point travel relative to each other;
    compensating the Q determined measure of microstructural status relative to the temperature of the sample material;
    obtaining mean temperature-compensated Q determined measures by averaging a number of successive temperature-compensated Q determinations;
    obtaining the standard deviation of the temperature-compensated Q determination for a number of successive temperature-compensated Q determinations;
    determining mean grain size, grain geometry, or grain orientation by using mean temperature-compensated Q determinations;
    determining frequency of inclusions or uniformity of coatings by using the standard deviation of temperature-compensated Q determinations; and
    varying at least one process parameter in response to the determined mean grain size of at least one depth to control grain size for at least one depth.

2. The method of claim 1 wherein the differential impedance (Z) of the LC circuit while inductively coupled to the sample material at the test point is used as the dependent variable in determining the microstructural status of the material.

3. The method of claim 1 wherein the differential lifetime expressed by the exponential response decay parameter, $\gamma$, to a pulse of sinusoidal radio frequency energy at the center frequency of the LC resonator circuit while inductively coupled to the sample material at the test point is used as a dependent variable in determining the microstructural status of the material.

4. The method of claim 1 wherein the LC resonator center frequency can be modified to allow sinusoidal radio frequency drive signals of different frequencies and thus sample material penetration depth, and hence the effective depth of microstructural measurement.

5. The method of claim 1 is further characterized in that said material is a material having a grain size gradient and the increment of the varying comprises controlling the grain size gradient responsive to determinations of the mean grain size.

6. The method of claim 5 wherein the grain geometry gradient and the increment of varying comprises the responsive parameter of control.

7. The method of claim 5 wherein the grain orientation gradient and the increment of varying comprises the responsive parameter of control.

8. The method of claim 1 is further characterized in that said material is a material having a distribution of inclusions and the increment of varying comprises controlling the frequency of inclusions responsive to determinations of the standard deviations of the microstructural status.

9. The method of claim 8 wherein the uniformity of a coating and the increment of varying comprises the responsive parameter of control.

10. The method of claim 8 wherein the uniformity of lines scribed in the surface of said material or coating perpendicular to the rolling direction and the increment of varying comprises the responsive parameter of control.

11. The method of claim 8 wherein the uniformity of selective coating ablation and the increment of varying comprises the responsive parameter of control.

12. The method of claim 8 wherein the uniformity of surface ablation and the increment of varying comprises the responsive parameter of control.

13. Apparatus for the in situ monitoring and process control of polycrystalline ferritic microstructure in materials comprising:
    means for moving the materials to a specified test point;
    means for inductively coupling the material to an LC resonator by a pure sinusoidal radio frequency electromagnetic field at the specified test point;
    means for measuring the difference in energy dissipation produced by inductively coupling the material to the LC resonator at the test point;
    means for determining the microstructural status of the material using the differential quality factor (Q) of the LC resonator while inductively coupled to the sample material at the test point;
    means for determining the temperature of the sample material by non-contacting sensor at the test point;
    means for compensating the Q determined measure of microstructural status relative to the temperature of the sample material;

means for averaging a number of successive temperature-compensated Q measures;

means for obtaining the standard deviation of a number of successive temperature-compensated Q measures;

means for calculating average grain size, grain geometry, or grain orientation from temperature-compensated averaged Q measures;

means for calculating the frequency of inclusions or uniformity of coating from the standard deviation of average temperature-compensated Q measures;

means for controlling at least one processed parameter in response to the Q determined average grain size of at least one depth to control the grain size for at least one depth.

14. The apparatus of claim 13 wherein the differential impedance (Z) of the LC circuit while inductively coupled to the sample material at the test point comprises the dependent variable in determining the microstructural status of the material.

15. The apparatus of claim 13 wherein the differential value of the exponential response decay parameter, $\gamma$, to a sinusoidal radio frequency energy at the center frequency of the LC resonator while inductively coupled to the sample at the test point comprises the dependent variable in determining the microstructural status of the material.

16. The apparatus of claim 13 wherein the LC resonator center frequency can be modified to determine the effective depth of microstructural measurement.

17. The apparatus of claim 13 wherein said material has a grain size gradient and wherein the means for controlling controls the grain size gradient responsive to determination of average grain diameter.

18. The apparatus of claim 13 wherein said material has a grain geometry gradient and wherein the means for controlling controls the grain geometry gradient responsive to determination of average grain geometry.

19. The apparatus of claim 13 wherein said material has a grain orientation gradient and wherein the means for controlling controls the grain orientation gradient responsive to determination of average grain orientation.

20. The apparatus of claim 13 is further characterized in that said material is a material having a distribution of inclusions and wherein the means for controlling controls the frequency of inclusions responsive to determination of standard deviations of the Q determined microstructural status.

21. The apparatus of claim 20 wherein a coating on said material has a gradient of uniformity and wherein the means for controlling controls the gradient of uniformity.

22. The apparatus of claim 20 wherein lines scribed on the surface of said material or coating on said material perpendicular to the rolling direction have a gradient of uniformity and wherein the means for controlling controls the gradient of uniformity.

23. The apparatus of claim 20 wherein the selective coating ablation of said material has a gradient of uniformity and wherein the means for controlling controls the gradient of uniformity.

24. The apparatus of claim 20 wherein the surface ablation of said material has a gradient of uniformity and wherein the means for controlling controls the gradient of uniformity.

25. The apparatus of claim 13 wherein the LC resonator comprises a pair of thin film $Y_1B_2C_3O_7$ planar inductors separated by a dielectric substrate.

26. The apparatus of claim 25 wherein the LC resonator is maintained at superconducting temperatures.

* * * * *

UNITED STATES PATENT AND TRADEMARK OFFICE
CERTIFICATE OF CORRECTION

PATENT NO. : 5,420,518  
DATED : May 30, 1995  
INVENTOR(S) : Kenneth L. Schafer, Jr.

It is certified that error appears in the above-indentified patent and that said Letters Patent is hereby corrected as shown below:

Title page, under section [56] References Cited, OTHER PUBLICATIONS, in the third reference, "Electrical Steels;" should read --Electrical Steels:--.

Abstract Lines 17-18 "condition" should read --conditions--.

Column 2 Line 20 "½th" should read --⅛th--.

Column 2 Line 26 "invent ion" should read --invention--.

Column 2 Line 65 "number microseconds." should read --number of microseconds.--.

Column 4 Line 18 "IEE" should read --IEEE--.

Column 4 Line 25 "et. al." should read --et al.--.

Column 4 Line 48 "et. al.," should read --et al.,--.

UNITED STATES PATENT AND TRADEMARK OFFICE
CERTIFICATE OF CORRECTION

PATENT NO. : 5,420,518
DATED : May 30, 1995
INVENTOR(S) : Kenneth L. Schafer, Jr.

It is certified that error appears in the above-indentified patent and that said Letters Patent is hereby corrected as shown below:

Column 5 Line 8 " et. al.," High " should read --et al., "High--.

Column 5 Line 52 "$f_H26$" should read --$f_H$ 26--.

Column 8 Line 1 "tile" should read --the--.

Column 8 Line 2 "slew" should read --slue--.

Column 8 Line 43 "$d_v5.$" should read --$d_v$ 5.--.

Column 9 Line 13 "$\times10^{-3})$" should read --$\times10^{-3})Q$--.

Signed and Sealed this

Twenty-first Day of November, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,420,518
DATED : May 30, 1995
INVENTOR(S) : Kenneth L. Schafer, Jr.

It is certified that error appears in the above-indentified patent and that said Letters Patent is hereby corrected as shown below:

Column 9 Line 12 "$(8.6363 \times 10^{-3})$" should read
-- $(8.6363 \times 10^{-3})Q$ --.

Signed and Sealed this

Twenty-fourth Day of December, 1996

Attest:

BRUCE LEHMAN

*Attesting Officer*  *Commissioner of Patents and Trademarks*